United States Patent [19]
Nelson et al.

[11] Patent Number: 5,657,767
[45] Date of Patent: Aug. 19, 1997

[54] DUAL JACKET ANKLE BRACE

[75] Inventors: Ronald E. Nelson, Chetek, Wis.; Karl E. Bjornson, Canton, Ohio

[73] Assignee: Tamarack International, Inc., Chetek, Wis.

[21] Appl. No.: 689,502

[22] Filed: Aug. 7, 1996

[51] Int. Cl.⁶ ............................................. A61F 5/37
[52] U.S. Cl. ................................. 128/882; 602/27
[58] Field of Search ........................... 128/845, 846, 128/882, 892, 893; 602/23, 27, 60, 61, 65; 36/89, 90; 2/2, 22

[56] References Cited

U.S. PATENT DOCUMENTS

| | | | |
|---|---|---|---|
| 4,313,433 | 2/1982 | Cramer | 602/27 |
| 4,323,058 | 4/1982 | Detty | 602/27 |
| 4,527,556 | 7/1985 | Nelson | 602/27 |
| 4,724,847 | 2/1988 | Nelson | 602/27 |
| 4,878,504 | 11/1989 | Nelson | 602/27 |
| 4,878,505 | 11/1989 | Thanner | 128/882 |
| 5,007,417 | 4/1991 | Bender | 602/27 |

*Primary Examiner*—Michael A. Brown
*Attorney, Agent, or Firm*—Nawrocki, Rooney & Sivertson

[57] ABSTRACT

A dual jacket ankle brace including a first set of lateral and medial sides are interconnected anteriorly, posteriorly, and at their bottom to form an inner jacket adapted to receive a foot and ankle. An anterior edge on each of these sides contains a set of lace receiving means such as eyelets. A second, outer set of medial and lateral sides overlie the inner lateral and medial sides. Each of the outer sides carries lace-receiving means such as eyelets. At least some of the eyelets on the outer sides are posteriorly spaced from and unaligned with any of the eyelets on the inner sides. Each of the inner lateral and medial sides also carries a pocket adapted to receive an insert, the outer lateral and medial sides overlying the respective pockets.

23 Claims, 2 Drawing Sheets

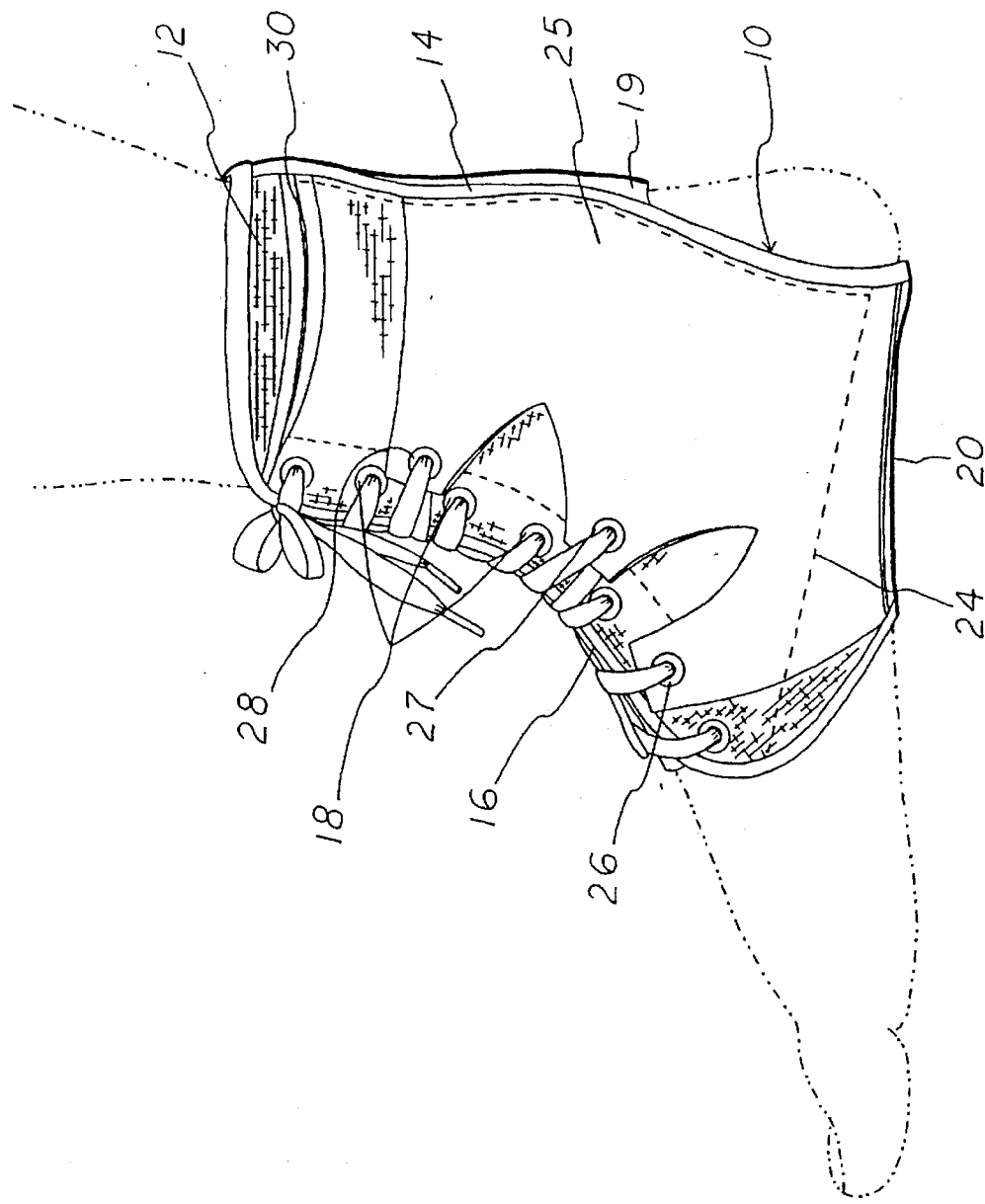
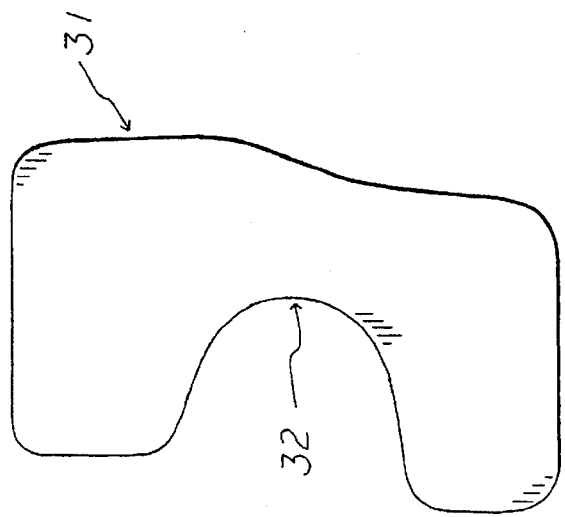
FIG. 2
FIG. 3

DUAL JACKET ANKLE BRACE

BACKGROUND OF THE INVENTION

1. Field of the Invention

The present invention relates generally to orthopedic devices, more particularly to localized support devices for the human body, and still more particularly to ankle braces.

Ankle braces are well-known in the prior art. Typically, such braces area formed of base members which may be made from, or include, flexible and/or elastic panels and which employ a variety of straps, stays and laces.

These braces are designed for a variety of circumstances such as supporting an ankle (healthy or damaged) during athletic competitions, providing chronic support for weak ankles or to aid during rehabilitation of acute injuries. In some instances, it is desirable to provide an external heel lock.

One known prior art ankle brace employs a first set of medial and lateral side members interconnected to form a base member in the form of a jacket adapted to receive a foot and ankle. A front or anterior edge on each of the side members contains eyelets laced in a normal fashion to enable the jacket to be secured by normal lacing. Another set of medial and lateral sides are connected to the outer portion of the jacket. The outer side members also have an anterior or front edge which carries a set of eyelets aligned with and positioned posterior to eyelets of the first side members. When the described prior art ankle brace is laced, the lace passes through the aligned eyelets of the first and outer side members on one side (medial or lateral) before crossing to pass through aligned side member eyelets on the other (medial or lateral) side. Eyelet alignment facilitates this concurrent or serial lacing of eyelets of the first and outer side members. The posterior position of the eyelets on the outer side members is intended to provide a tension in the outer side members which is not limited by the tension applied to the first side members. The result, however, is to limit the tension applied to the first side members. Thus, the concurrant lacing of first and outer side members results in an interdependent tension beyond the interdependence inherent in the use of a common lace. Further, the concurrent lacing of this prior art brace limits the amount of posterior offset of the outer side member eyelets from the first side member eyelets—too great an offset results in little or no tension on the first side members.

SUMMARY OF THE INVENTION

For a successful heel lock, a brace must: squeeze the medial and lateral malleoli together; push the calcaneus and talus up into the ankle mortise; and capture the calcaneus to limit inversion and eversion. A device in accordance with the present invention can perform all of these functions to provide a successful heel lock.

An ankle brace in accordance with the present invention employs inner and center sets of medial and lateral side members to form a dual jacket. The anterior or front edges of the side members carry a set of eyelets, at least some of the eyelets of the outer side members being positioned posterior to the eyelets of the inner side members and in non-alignment with the eyelets of the inner side members. When laced, the lace passes through an eyelet of one of the medial side members (inner or outer) and passes to, and through, an eyelet of one of the lateral side members (inner or outer) and returns to, and through, a medial side member eyelet in a parallel lacing pattern of the inner and outer side member eyelets in the region of the non-aligned outer side member eyelets. This parallel lacing pattern (in contrast to the concurrent or serial lacing pattern of the prior art device described above) provides an independent tensioning of the inner and outer jackets and a reliable heel lock.

In preferred embodiments in accordance with the present invention, additional support is provided via a pocket on each of the inner side members (medial and lateral), the pockets being adapted to receive either flexible or semi-rigid inserts. When the outer sides are properly laced, they provide a direct pressure on the pockets containing the inserts, thus creating an additional positive support system.

BRIEF DESCRIPTION OF THE DRAWINGS

The objects of the present invention and many of the attendant advantages of the same will be readily appreciated as they become better understood by reference to the following detailed description when considered in connection with the accompanying drawings, in which drawings like reference numerals designate like parts through the figures and wherein:

FIG. 2 is a side plan view of the apparatus of FIG. 1 on a foot and ankle, which foot and ankle are shown in phantom lines; and FIG. 3 is a plan view of a pocket insert used in the apparatus of FIGS. 1 and 2.

DETAILED DESCRIPTION OF THE PREFERRED EMBODIMENTS

Figure 1:
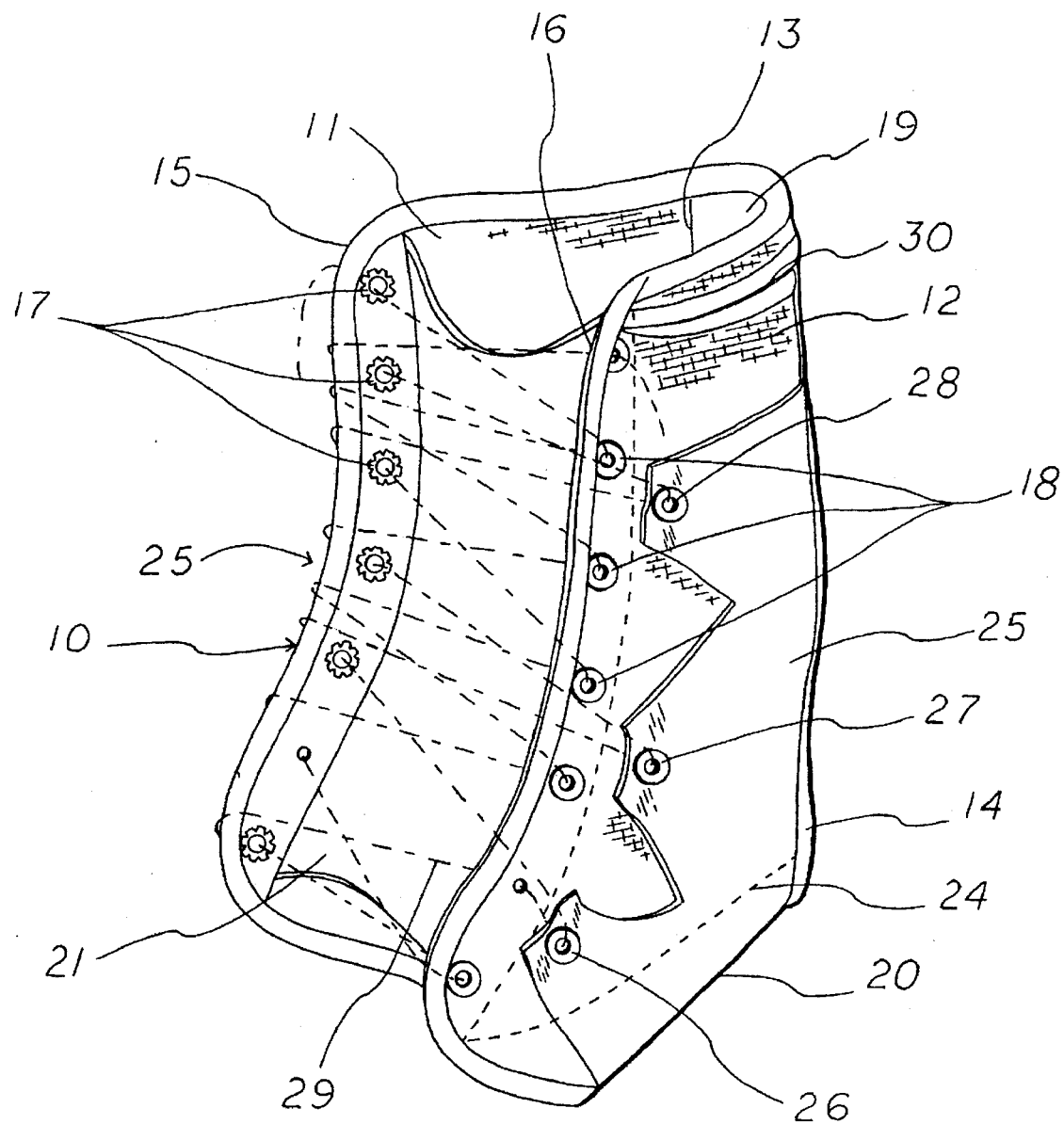
FIG. 1 is a perspective view of an ankle brace in accordance with the present invention, including a phantom line illustration of the brace lacing pattern.

The embodiment of present invention shown and described herein is ambidextrous—it fits either foot. However, for purposes of description, the present invention is described in the context of the right foot and ankle with terms such as medial and lateral being references relative to the right foot and ankle.

In FIG. 1 there is shown a dual jacket brace 10 in accordance with the present invention. The brace 10 includes an inner lateral side member or panel 11 and an inner medial side member or panel 12. Lateral side member 11 includes an inner lateral posterior edge 13 and an inner lateral anterior edge 15. Medial side member 12 includes an inner medial posterior edge 14 (See FIG. 2) and an inner medial anterior edge 16. A set of lace receiving devices in the form of eyelets 17 is shown generally linearly disposed along edge 15, and another set of lace receiving devices in the form of eyelets 18 is shown generally linearly disposed along edge 16. The second from the bottom eyelet on each of edges 15 and 16 do not have grommets for reasons of bulk as will be apparent to those skilled in the art from the description herein.

Posterior edges 13 and 14 are joined together by an elastic web 19 sewn to each of edges 13 and 14. Similarly, the anterior portions of sides 11 and 12 are joined together by another elastic web 21 sewn to each of sides 11 and 12 at a point slightly posteriorly spaced from anterior edges 15 and 16. In this preferred embodiment, web 21 also serves as a tongue. Finally, the formation of the inner jacket of brace 10 is completed by sewing together the bottom edge 20 of inner side members 11 and 12.

Also shown in FIG. 1 is an outer medial side member 25 having a medial posterior edge collinear with the posterior edge 14 of inner medial side member 12. The anterior portion of outer medial side member 25 is cleft to define three eyelet tabs carrying eyelets 26, 27 and 28. The lowest eyelet 26 overlies and is aligned with a grommet-free eyelet of eyelet set 18, as described above. The middle eyelet 27 is spaced or offset posteriorly from the anterior edge 16 of eyelets 18 and is unaligned with any of eyelets 18. Upper eyelet 28 is similarly posteriorly spaced or offset from anterior edge 16 and eyelets 18 and is also unaligned with any of eyelets 18. Eyelets are aligned, in the sense that term is used herein, when one generally overlies the other or would overlie the other but for the displacement resulting from posterior offset. Conversely, eyelets are unaligned when they are not aligned—one would not generally overlie the other even if they were equidistantly spaced from the edge 16 or 15. For example, eyelet 27 would lie intermediate two of eyelets 18 if eyelet 27 were advanced toward edge 16 by the distance of its posterior offset and accordingly, is unaligned with those eyelets. It should be noted that one eyelet 18 lies intermediate eyelets 26 and 27 while intermediate eyelets 27 and 28 there are two of eyelets 18. Also, a lateral side member corresponding to side member 25 is provided to overlie side member 11 and corresponds in its details to side member 25.

When properly interlaced, (laces being shown in FIG. 2 and the lacing sequence being represented by dotted line 29 in FIG. 1), the lowest eyelet 26 on outer medial and lateral sides 25 will cooperate with lower most two eyelets 17 and 18 with which they are aligned to anchor side members 11, 12 and 25 to the foot. Offset and unaligned eyelets 27 and 28 function to provide a direct tension on outer medial and lateral sides 25 which will act to effect a heel lock on a foot and ankle within dual jacket brace 10 in conjunction with the tension applied in inner medial and lateral sides via eyelets 17 and 18. As illustrated by dotted line 29 in FIG. 1, with the exception of eyelets 26 and associated eyelets in inner side members 11 and 12, the lace passes through only one lateral or medial side eyelet before crossing to pass through an eyelet on the other lateral or medial side. Each eyelet 26 is "serially" laced with its associated eyelet 17 or 18 while eyelets 27 and 28 are "parallel" laced with respect to the eyelets 17 or 18 on their respective lateral or medial side. As shown in FIGS. 1 and 2, the tabs which carry the eyelets 26–28 are formed by V-shaped clefts in the outer side members 25. The use of tabs allows the outer jacket of side members 25 to lie flat when tensioned by the laces while the tabs are independently tensioned.

Finally, a pocket 30 is shown in inner side member 12, separate from outer side 25, but overlain by side member 25. Pocket 30 is adapted to receive a selected insert or stay such as that shown at 31 in FIG. 3 discussed below. A stay 31 inserted in pocket 30 will receive a direct pressure from overlying outer side 25 which, when tensioned by the laces, will provide a positive support pressure on the ankle being supported. It will be recognized that a similar insert receiving pocket exists on both the inner lateral and medial sides 11 and 12. Dotted line 24 in FIGS. 1 and 2 represents stitching which defines the sides and bottom of pocket 30.

In FIG. 3 there is shown a plan view of an insert or stay 31 formed as a flat plate. Insert 31 may be of a flexible material and placed in pocket 30 when it is the desire to provide increased ankle support for an acute injury or chronic weak ankles. Insert 31 may be of a more rigid or semi-rigid material when it is desired to provide a splinting support for maximum ankle stability for severely injured ankles, post-surgery rehabilitation and severe unstable ankles. Insert 31 includes an aperture 32 positioned to overlie the malleoli of the ankle being supported and is shaped to prevent undue pressure on the malleoli. It will further be recognized that the shape and use of insert 31 in pocket 30 of brace 10 of the apparatus of this invention are designed to give positive support to the ankle, but that many other forms of insert 31 may be used without departing from the spirit of this invention.

In a preferred embodiment, the inner jacket formed of panels 11 and 12 may be constructed of a foam backed material while the outer jacket of panels 27 may be formed of vinyl. Obviously, other materials may be employed within the functional requirements described. Also, while a preferred embodiment having a specific number of eyelets is described, a different number of eyelets, including outer jacket eyelets, may be employed without departing from the scope of the invention.

Having thus described the preferred embodiments of the present invention, those of skill in the art will readily appreciate other useful embodiments within the scope of the claims hereto attached.

What is claimed is:

1. In a dual jacket ankle brace of the type having an inner support jacket including medial and lateral side members and a plurality of lace receiving eyelets along the anterior edge of said inner support jacket side members and having an outer support jacket including medial and lateral side members and a plurality of lace receiving eyelets along the anterior edge of said outer support jacket side members, the improvement wherein at least some of said outer support jacket eyelets are posteriorly offset and unaligned relative to said inner support jacket eyelets.

2. The dual jacket ankle brace improvement of claim 1 wherein said outer support jacket medial and lateral side members are cleft along their anterior edge to define tabs.

3. The dual jacket ankle brace improvement of claim 2 wherein said tabs carry at least one of said outer support jacket eyelets.

4. The dual jacket ankle brace improvement of claim 1 wherein said inner support jacket medical and lateral side members include pocket means and further comprising stay means with said pocket means.

5. The dual jacket ankle brace improvement of claim 4 wherein said pocket means position said stay means over an respective malleoli when said brace is placed on an ankle.

6. The dual jacket ankle brace improvement of claim 5 wherein said stay means include a central aperture adopted to overlie said malleoli.

7. The dual jacket ankle brace improvement of claim 4 wherein the outer support jacket support members overlie the inner support jacket pocket means and stay means within said pocket means.

8. The dual jacket ankle brace improvement of claim 7 wherein said pocket means position said stay means over an respective malleoli when said brace is placed on an ankle.

9. The dual jacket ankle brace improvement of claim 8 wherein said pocket means position said stay means over an respective malleoli when said brace is placed on an ankle.

10. The dual jacket ankle brace improvement of claim 9 wherein said outer support jacket medial and lateral side members are cleft along their anterior edge to define tabs.

11. The dual jacket ankle brace improvement of claim 10 wherein said tabs carry at least one of said outer support jacket eyelets.

12. The dual jacket ankle brace improvement of claim 11 wherein said stay means are formed as a flat, flexible plate.

13. The dual jacket ankle brace improvement of claim 11 wherein said stay means are formed as a flat, semi-rigid plate.

14. The dual jacket ankle brace improvement of claim 11 wherein said brace is ambidextrous.

15. The dual jacket ankle brace improvement of claim 1 wherein said brace is ambidextrous.

16. Ankle brace apparatus comprising:

an inner support jacket including an inner medial side member and an inner lateral side member each having bottom, posterior and anterior edges, and means interconnecting said bottom edges and said posterior edges and said anterior edges; each of said inner side member anterior edges including a first plurality of lace receiving means; and an outer support jacket including an outer medial side member and an outer lateral side member each having bottom, posterior and anterior edges; means connecting said outer side member bottom edges to said inner side member, means connecting said outer side member posterior edges adjacent said inner side member posterior edges; each of said outer side member anterior edges including a second plurality of lace receiving means, said second plurality being a lesser number than said first plurality and at least a portion of said outer side member lace receiving means being posteriorly offset from and unaligned with said inner side member lace receiving means.

17. The apparatus of claim 16 including a pocket carried by each of said inner side members, each of said pockets being overlaid by the respective of said outer sides; and support inserts for placement in each of said pockets.

18. The apparatus of claim 17 in which said support inserts comprise flexible plates each having an aperture adapted to fit over the respective of said malleoli.

19. The apparatus of claim 17 in which said support inserts comprise semi-rigid plates each having an aperture adapted to fit over the respective of said malleoli.

20. The apparatus of claim 16 in which said lace receiving means comprise eyelets and said second plurality comprises three eyelets; the lowest of said second plurality of three eyelets being generally aligned with and overlying a lower eyelet of said first plurality; the middle and upper of said three eyelet plurality being posteriorly offset from and unaligned with any of said first plurality of eyelets.

21. The apparatus of claim 20 including a pocket carried by each of said inner side members, each of said pockets being overlaid by the respective of said outer sides; and support inserts for placement in each of said pockets.

22. The apparatus of claim 21 in which said support inserts comprise flexible plates each having an aperture adapted to fit over the respective of said malleoli.

23. The apparatus of claim 21 in which said support inserts comprise semi-rigid plates each having an aperture adapted to fit over the respective of said malleoli.

* * * * *